US006448420B1

(12) United States Patent
Kinsho et al.

(10) Patent No.: US 6,448,420 B1
(45) Date of Patent: *Sep. 10, 2002

(54) ACID-DECOMPOSABLE ESTER COMPOUND SUITABLE FOR USE IN RESIST MATERIAL

(75) Inventors: Takeshi Kinsho; Tsunehiro Nishi; Takeru Watanabe; Koji Hasegawa; Mutsuo Nakashima; Jun Hatakeyama, all of Niigata-ken (JP)

(73) Assignee: Shin-Etsu Chemical Co., Ltd. (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/572,975

(22) Filed: May 18, 2000

(30) Foreign Application Priority Data

May 19, 1999 (JP) ............................................. 11-138090

(51) Int. Cl.$^7$ .............................. C07J 9/00; C07C 69/74
(52) U.S. Cl. ........................................... 552/549; 560/1
(58) Field of Search ................................ 552/553, 549; 560/1

(56) References Cited

U.S. PATENT DOCUMENTS

| 6,030,746 A | 2/2000 | Nagata et al. |
| 6,048,661 A | 4/2000 | Hatakeyama et al. |

FOREIGN PATENT DOCUMENTS

| EP | 0 646 568 | 4/1995 |
| EP | 0 918 048 | 5/1999 |
| JP | 9-278699 | 10/1997 |

OTHER PUBLICATIONS

Popova et al., Chemical Abstracts, vol. 118(3), Jan. 18, 1993, p. 711.*
Lenoir et al., J. Org. Chem., vol. 53(3), pp. 661–675, 1988.*
127:364169 CA abstract of JP 09–265177, Oct. 1997.
Translation of JP 09–265177, Oct. 1997.
Janusz J M et al: "High Potency Dipeptide Sweetners. 1. L–Aspartly–D–Phenylglycine Esters" Journal of Medicinal Chemistry, American Chemical Society, vol. 13, No. 3, Mar. 1, 1990 pp. 1052–1061.
Banert K et al: Chemische Berichte., vol. 116, No. 11, 1983, pp. 3591–3610.
Brown H C et al: Journal of the American Chemical Society., vol. 90, No. 10, 1968 pp. 2691–2693.
Roberts J D et al: Journal of the American Chemical Society., vol. 75, 1953 pp. 3165–3168.
Johansson A et al: "A Short and Selective Synthesis of (S)–Geranylcitronellol via Conjugate Addition of a Functionalized Copper Reagent to 2–Substituted Exo–Bornyl Crotonates" Tetrahedron Letters, NL, vol. 37, No. 39 Sep. 23, 1996.
Bergdahl M et al.: Tetrahedron, vol. 47, No. 46, 1991, pp. 9691–9702.
Olsson T et al: Tetrahedron., vol. 46, No. 7, 1990, pp. 2473–2482.
Olsson T et al: Journal of Organic Chemistry., vol. 53, No. 11, 1988, pp. 2468–2472.
Bohlman C et al: Liebigs Annalen der Chemie., vol. 9, 1985, pp. 1752–1763.
Hueckel; Justus Liebigs Annalen der Chemie., vol. 549, 1941.
Hueckel et al; Justus Liebigs Annalen der Chemie., vol. 585, 1954.
Chemical Abstracts, vol. 119, No. 4, Jul. 26, 1993 Chen et al; p. 413.
Chemical Abstracts, vol. 118, No. 3, Jan. 18, 1993 Popova et al; p. 711.
Ludwick A G et al; Journal of Organic Chemistry, vol. 34, 1969, pp. 4108–4115.
Toivonen N J et al; Anales Academiae Scientiarum Fennicae Series A II, vol. 64, 1955, pp. 3–11 Helsinki Finland.
English Abstract for JP 6–266109.

* cited by examiner

Primary Examiner—Barbara P. Badio
(74) Attorney, Agent, or Firm—Millen, White, Zelano & Branigan, P.C.

(57) ABSTRACT

A novel ester compound having an exo-form 2-alkylbicyclo [2.2.1]heptan-2-yl ester as the acid-decomposable site is used as a dissolution regulator to formulate a resist composition having a high sensitivity, resolution, etching resistance and storage stability.

5 Claims, No Drawings

ACID-DECOMPOSABLE ESTER COMPOUND SUITABLE FOR USE IN RESIST MATERIAL

BACKGROUND OF THE INVENTION

1. Field of the Invention

The present invention relates to a novel acid-decomposable ester compound suitable for use in a resist material.

2. Prior Art

While a number of recent efforts are being made to achieve a finer pattern rule in the drive for higher integration and operating speeds in LSI devices, deep-ultraviolet lithography is thought to hold particular promise as the next generation in microfabrication technology. In particular, photolithography using a KrF or ArF excimer laser as the light source is strongly desired to reach the practical level as the micropatterning technique capable of achieving a feature size of 0.3 μm or less.

For resist materials for use with KrF excimer lasers, polyhydroxystyrene having a practical level of transmittance and etching resistance is, in fact, a standard base resin. For resist materials for use with ArF excimer lasers, polyacrylic or polymethacrylic acid derivatives and polymers comprising aliphatic cyclic compounds in the backbone are under investigation. In either case, the basic concept is that some or all of alkali soluble sites of alkali soluble resin are protected with suitable acid-eliminatable groups. The overall performance of resist material is adjusted by a choice from among a variety of acid-eliminatable protective groups or by incorporating one or more low-molecular-weight components having an appropriate function separate from the resin.

One typical functional low-molecular-weight component to be formulated in resist materials is a class of compounds known as dissolution regulators. A variety of proposals have been made on the structure of dissolution regulators. A common structure has on a mother nucleus of a certain size one or plural readily alkali-soluble sites, some or all of which are blocked with acid-decomposable protective groups (see JP-A 6-266109 and JP-A 9-278699). When an appropriate amount of dissolution regulator is blended, the dissolution of the resist film in the unexposed area is restrained whereas in the exposed area, readily alkali-soluble sites which are exposed under the action of generated acid promote the dissolution of the resist film. That is, the differential dissolution rate between the exposed and unexposed areas is enhanced. Consequently, the resolution of the resist film is considerably improved.

What is required for the dissolution regulator is to keep low the dissolution rate of the resist film in the unexposed area and to allow the exposed area to quickly turn to be readily soluble in an alkali developer. These properties are largely affected by the mother nucleus and the choice of acid-decomposable sites. For the mother nucleus, sufficient hydrophobicity is essential for exerting dissolution inhibition in the unexposed area, and the mother nucleus must also have such a structure that developer affinity is insured in deblocked form for exerting dissolution promotion in the exposed area. Also, the acid-decomposable sites are required to have contradictory properties in that the acid-decomposable sites must have a high reactivity sufficient to quickly decompose even in low exposed area such as resist film deep inside, whereas they must have a low reactivity sufficient to prevent reaction from being triggered merely by exposure and a stability sufficient to prevent a sensitivity variation during storage, in order to restrain the formation of volatile decomposition products which can contaminate the optical system of an aligner. As to the mother nucleus, it is relatively easy to design the mother nucleus having hydrophobicity and developer affinity upon deblocking adequate to the purpose, by increasing the molecular weight above a certain level and optionally incorporating a cyclic structure. However, the acid-decomposable sites that fully satisfy the requirement are not yet available.

As to the currently available acid-decomposable sites, tertiary alkyl esters such as tert-butyl esters and 1-alkoxyalkyl esters such as 2-tetrahydropyranyl esters and 1-ethoxyethyl esters are known as the protected carboxylic acid; tertiary alkyl carbonates such as tert-butyl carbonate, tertiary alkyl ethers such as tert-butyl ethers, and 1-alkoxyalkyl ethers such as 2-tetrahydropyranyl ethers and 1-ethoxyethyl ethers are known as the protected phenolic hydroxyl group. Among the foregoing examples, however, the 1-alkoxyalkyl esters and 1-alkoxyalkyl ethers are excessively reactive and have the risk of causing contamination of the aligner optical system and sensitivity variation. Inversely, the remaining examples are poorly reactive and fail to fully accelerate the dissolution rate in the exposed area. In addition, many other proposals have been made on the acid-decomposable sites although they are not satisfactory in both reactivity and stability. While the pattern rule is increasingly scaled down, there is a need to have a dissolution regulator having improved acid-decomposable sites and a high sensitivity, high resolution resist material which can be realized thereby.

SUMMARY OF THE INVENTION

Therefore an object of the present invention is to provide a novel acid-decomposable ester compound which has both high reactivity and sufficient storage stability and which when blended as a dissolution regulator, form a resist material having high sensitivity and resolution.

It has been found that an ester compound of the following general formula (1) obtained by a method to be described later is useful as a dissolution regulator to be blended in a resist material. The resist material having the ester compound blended therein has high sensitivity and resolution and is suited for precise microfabrication.

The invention provides an ester compound of the following general formula (1).

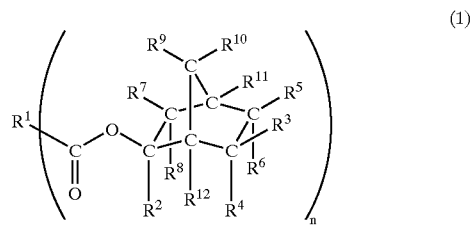

Herein $R^1$ is an n-valent hydrocarbon group of 4 to 40 carbon atoms having a saturated alicyclic structure or aromatic ring structure which may contain a hetero atom. $R^2$ is a straight, branched or cyclic alkyl group of 1 to 8 carbon atoms or a substituted or unsubstituted aryl group of 6 to 20 carbon atoms. $R^3$ to $R^{12}$ each are hydrogen or a monovalent hydrocarbon group of 1 to 15 carbon atoms which may contain a hetero atom and $R^3$ to $R^{12}$, taken together, may form a ring, and when they form a ring, they represent divalent hydrocarbon groups of 1 to 15 carbon atoms which may contain a hetero atom, or two of $R^3$ to $R^{12}$ which are attached to adjacent carbon atoms may directly bond together to form a double bond. The letter n is an integer of 1 to 8. The formula also represents an enantiomer.

Preferably in formula (1), $R^1$ is an n-valent hydrocarbon group of 4 to 40 carbon atoms, in which n hydrogen atoms at arbitrary positions are eliminated to introduce valence bonds, selected from among (i) alicyclic saturated hydrocarbons including

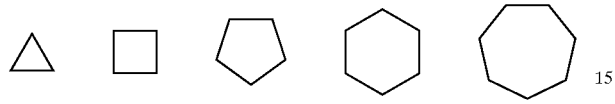
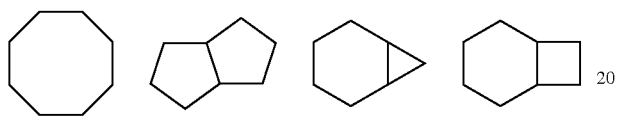
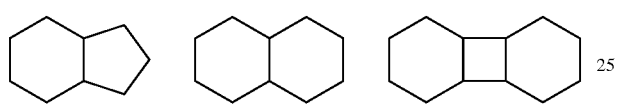
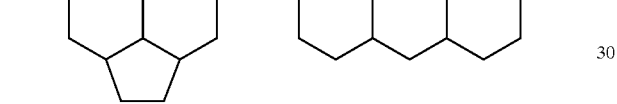
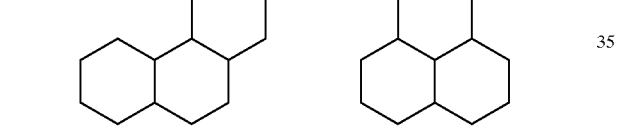
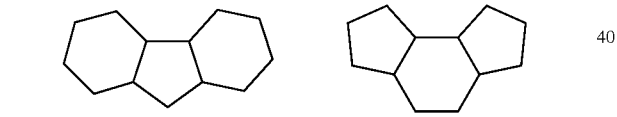
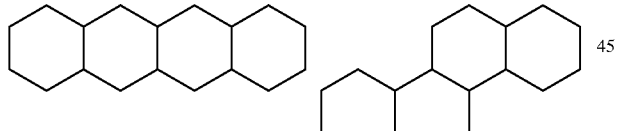
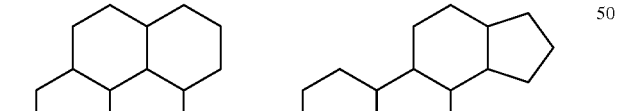
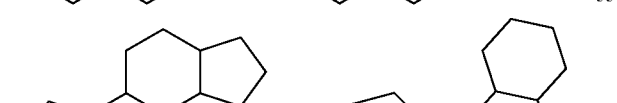
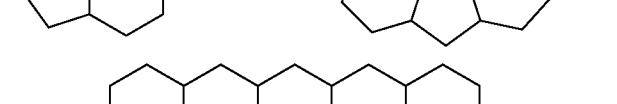
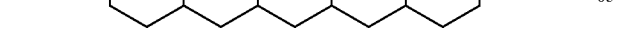

-continued

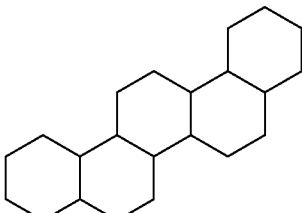
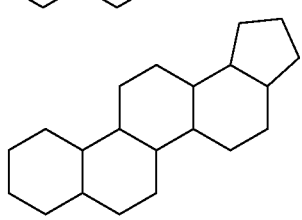
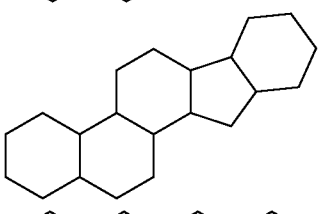
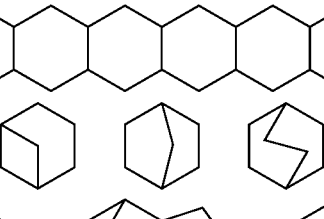
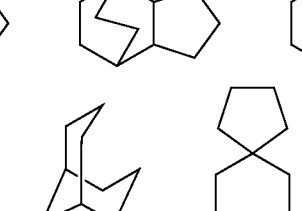
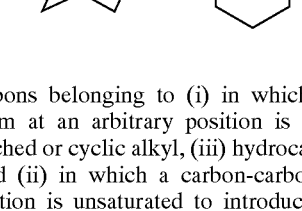
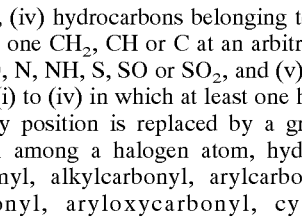

(ii) hydrocarbons belonging to (i) in which at least one hydrogen atom at an arbitrary position is replaced by a straight, branched or cyclic alkyl, (iii) hydrocarbons belonging to (i) and (ii) in which a carbon-carbon bond at an arbitrary position is unsaturated to introduce at least one aromatic ring, (iv) hydrocarbons belonging to (i) to (iii) in which at least one $CH_2$, CH or C at an arbitrary position is replaced by O, N, NH, S, SO or $SO_2$, and (v) hydrocarbons belonging to (i) to (iv) in which at least one hydrogen atom at an arbitrary position is replaced by a group of atoms selected from among a halogen atom, hydroxyl, alkoxy, aryloxy, formyl, alkylcarbonyl, arylcarbonyl, carboxy, alkoxycarbonyl, aryloxycarbonyl, cyano, amino, alkylamino, arylamino, mercapto, alkylthio, arylthio, carbamoyl, alkylcarbamoyl, arylcarbamoyl, alkylcarbonylamino, arylcarbonylamino, sulfo, oxo, and imino group or an alkyl or aryl containing said group of atoms;

$R^2$ is a straight, branched or cyclic alkyl group of 1 to 8 carbon atoms or an aryl group of 6 to 20 carbon atoms which may be substituted with an alkyl group;

$R^3$ to $R^{12}$ are independently hydrogen, or straight, branched or cyclic alkyl groups of 1 to 15 carbon atoms which may be substituted with a group of atoms selected from among a halogen atom, hydroxyl, alkoxy, aryloxy, formyl, alkylcarbonyl, arylcarbonyl, carboxy, alkoxycarbonyl, aryloxycarbonyl, cyano, amino, alkylamino, arylamino, mercapto, alkylthio, arylthio, carbamoyl, alkylcarbamoyl, arylcarbamoyl, alkylcarbonylamino, arylcarbonylamino, sulfo, oxo, and imino group, a pair of $R^3$ and $R^4$, a pair of $R^3$ and $R^5$, a pair of $R^4$ and $R^6$, a pair of $R^5$ and $R^6$, a pair of $R^5$ and $R^7$, a pair of $R^5$ and $R^{10}$, a pair of $R^5$ and $R^{11}$, a pair of $R^6$ and $R^8$, a pair of $R^6$ and $R^{11}$, a pair of $R^7$ and $R^8$, a pair of $R^7$ and $R^9$, a pair of $R^7$ and $R^{11}$, a pair of $R^8$ and $R^{11}$, a pair of $R^9$ and $R^{10}$, a pair of $R^9$ and $R^{11}$, and a pair of $R^{10}$ and $R^{11}$ each may form a ring, and when these R's form a ring, they are independently straight, branched or cyclic alkylene groups of 1 to 15 carbon atoms which may be substituted with a group of atoms selected from among a halogen atom, hydroxyl, alkoxy, aryloxy, formyl, alkylcarbonyl, arylcarbonyl, carboxy, alkoxycarbonyl, aryloxycarbonyl, cyano, amino, alkylamino, arylamino, mercapto, alkylthio, arylthio, carbamoyl, alkylcarbamoyl, arylcarbamoyl, alkylcarbonylamino, arylcarbonylamino, sulfo, oxo, and imino group, or a pair of $R^3$ and $R^5$, a pair of $R^5$ and $R^{11}$, a pair of $R^7$ and $R^{11}$, and a pair of $R^9$ and $R^{11}$ may form a single bond so that a double bond is formed between the carbon and the carbon to which these R's are attached.

The ester compound of formula (1) employs an exo-form 2-alkylbicyclo[2.2.1]heptan-2-yl ester or derivative thereof as the acid-decomposable site, thereby overcoming the problems including the tert-butyl esters, tert-butyl carbonate and tert-butyl ethers having low reactivity as well as the 2-tetrahydropyranyl esters, 1-ethoxyethyl esters, 2-tetrahydropyranyl ethers and 1-ethoxyethyl ethers having excessive reactivity, when used as a dissolution regulator in a resist material.

The ester compounds of formula (1) are broadly classified as alkylcycloalkyl esters. The alkylcycloalkyl esters being basically tertiary alkyl esters are free of the drawback of excessive acidolysis; when formulated into resist materials, they do not allow reaction from taking place merely by exposure to form volatile decomposition products within the aligner or undergo decomposition during storage; nevertheless, they have higher acidolysis than simple tertiary alkyl esters such as tert-butyl esters. For these reasons, the alkylcycloalkyl esters belong to a relatively satisfactory class of acid-decomposable sites on the dissolution regulator for use in resist materials. The ester compounds of formula (1) for use in resist materials are successful in significantly enhancing acidolysis without compromising the advantages of the alkylcycloalkyl esters. The reason is given below.

Decomposition reaction of tertiary alkyl esters under acidic conditions proceeds by way of El mechanism. Those esters having a more stable carbocation under transition conditions have a higher rate of reaction and hence, a higher rate of decomposition. In the exo-form 2-alkylbicyclo[2.2.1] heptan-2-yl esters of formula (1), probably because of a-participation, a very stable cation is formed as shown by the reaction scheme below, and thus the progress of reaction is very rapid. This is a reaction inherent to the exo-form compound of formula (1). Little or no reaction occurs with an isomer or an endo-form compound of the following formula (1'). The compounds of formulae (1) and (1'), which look alike when expressed in plan structure, have largely different rates of acid decomposition reaction. Accordingly, the compound of formula (1), the compound of formula (1'), and the compound of formula (1") expressed with no stereostructure taken into account must be recognized, in fact, to be completely different substances (see Y. Yukawa Ed., Theory of Organic Chemistry -Reaction-, Kagaku Dojin Publishing, 1974, Chap. 8).

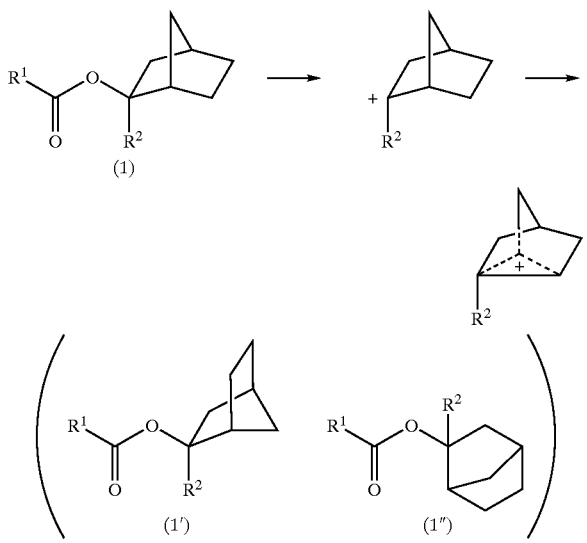

Herein, $R^1$ to $R^{12}$ and n are as defined above although $R^3$ to $R^{12}$ and n are omitted for the brevity of description.

Because of the above-described mechanism, the exo-form 2-alkylbicyclo[2.2.1]heptan-2-yl esters of formula (1) have an acid decomposition ability that outstandingly surpasses not only simple tertiary alkyl esters, but also alkylcycloalkyl esters and prior art fused ring-containing alkylcycloalkyl esters having not considered stereochemistry. Therefore, the resist composition comprising the inventive compound as a dissolution regulator becomes a very high sensitivity, high resolution resist material as compared with prior art resist materials, as will be later demonstrated in Examples.

Although the compounds of formula (1) have been arrived at originally from efforts in pursuit of acid decomposition, quite unexpectedly, they have some advantages in addition to high reactivity. Such advantages are a large polarity change due to the high hydrophobic nature of an eliminatable portion of the acid eliminatable site, and a very high rigidity that bicyclo[2.2.1]heptane skeleton possesses. Because of these excellent characteristics, the resist material having blended therein the ester compound of the invention has a very high etching resistance as well as a high sensitivity and high resolution.

The ester compounds of formula (1) have been arrived at by making investigations on acid elimination reaction from the aspect of stereochemistry. In this sense, the present invention is based on a concept utterly different from the prior art improvement in acid eliminatable sites that was discussed solely from the standpoint of plane structure. The invention is clearly distinguishable from the prior art proposals of novel acid eliminatable sites.

DETAILED DESCRIPTION OF THE INVENTION

The ester compound of the invention is of the general formula (1).

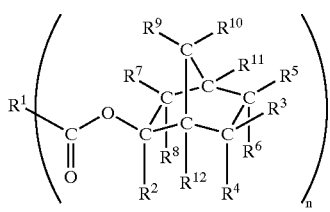

(1)

$R^1$ is an n-valent $C_{4-40}$ hydrocarbon group having a saturated alicyclic structure or aromatic ring structure which may contain a hetero atom wherein n is an integer of 1 to 8.

More illustratively, $R^1$ is an n-valent $C_{4-40}$ hydrocarbon group, in which n hydrogen atoms at arbitrary positions are eliminated to introduce valence bonds, selected from among (i) alicyclic saturated hydrocarbons including

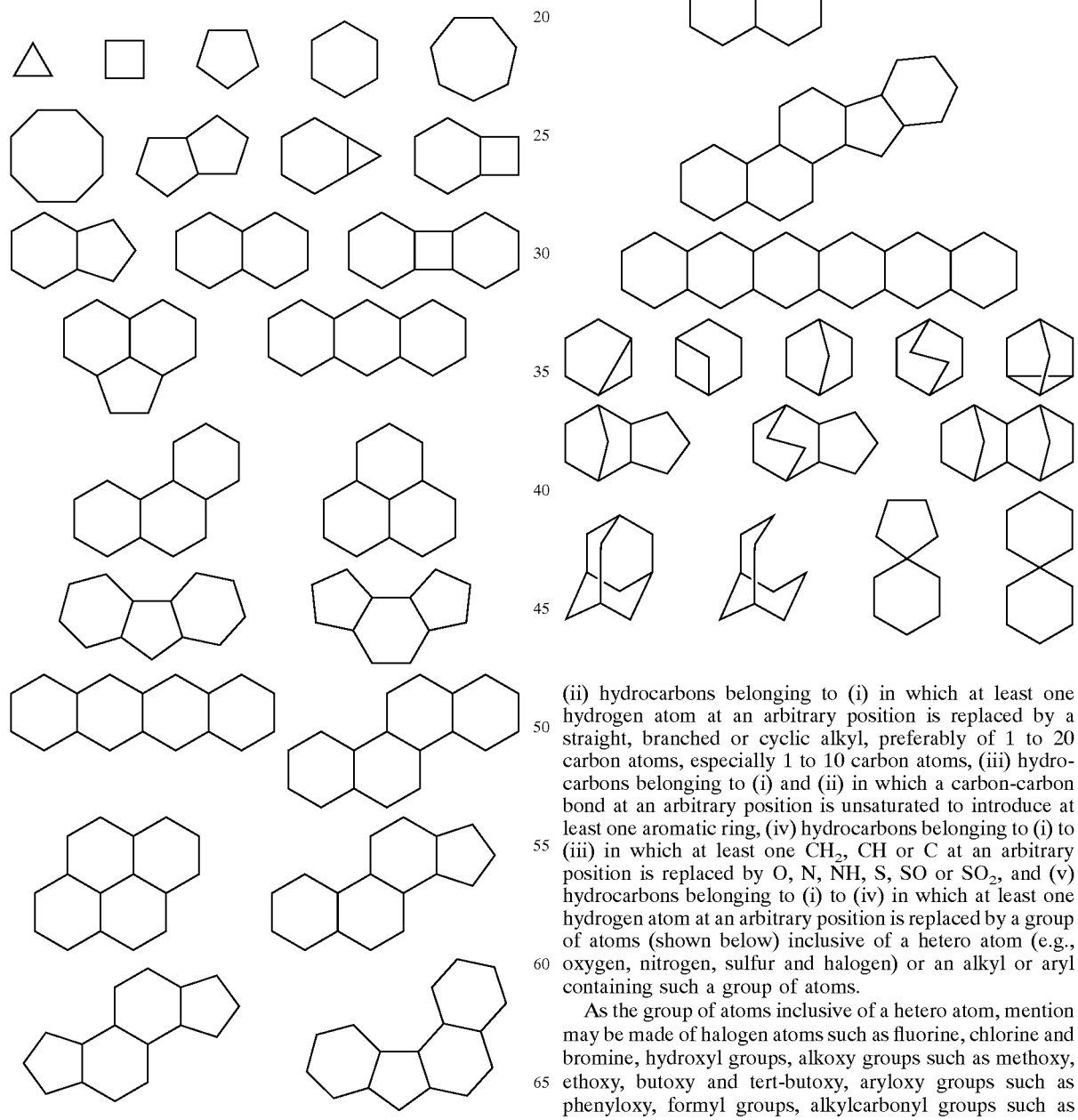

(ii) hydrocarbons belonging to (i) in which at least one hydrogen atom at an arbitrary position is replaced by a straight, branched or cyclic alkyl, preferably of 1 to 20 carbon atoms, especially 1 to 10 carbon atoms, (iii) hydrocarbons belonging to (i) and (ii) in which a carbon-carbon bond at an arbitrary position is unsaturated to introduce at least one aromatic ring, (iv) hydrocarbons belonging to (i) to (iii) in which at least one $CH_2$, CH or C at an arbitrary position is replaced by O, N, NH, S, SO or $SO_2$, and (v) hydrocarbons belonging to (i) to (iv) in which at least one hydrogen atom at an arbitrary position is replaced by a group of atoms (shown below) inclusive of a hetero atom (e.g., oxygen, nitrogen, sulfur and halogen) or an alkyl or aryl containing such a group of atoms.

As the group of atoms inclusive of a hetero atom, mention may be made of halogen atoms such as fluorine, chlorine and bromine, hydroxyl groups, alkoxy groups such as methoxy, ethoxy, butoxy and tert-butoxy, aryloxy groups such as phenyloxy, formyl groups, alkylcarbonyl groups such as methylcarbonyl and tert-butylcarbonyl, arylcarbonyl groups such as phenylcarbonyl, carboxy groups, alkoxycarbonyl groups such as methoxycarbonyl and tert-butoxycarbonyl, aryloxycarbonyl groups such as phenyloxycarbonyl, cyano groups, amino groups, alkylamino groups such as methylamino and dimethylamino, arylamino groups such as phenylamino and diphenylamino, mercapto groups, alkylthio groups such as methylthio, arylthio groups such as phenylthio, carbamoyl groups, alkylcarbamoyl groups such as dimethylcarbamoyl, arylcarbamoyl groups such as diphenylcarbamoyl, alkylcarbonylamino groups such as methylcarbonylamino, arylcarbonylamino groups such as phenylcarbonylamino, sulfo groups, oxo groups, and imino groups. Also included are alkyl groups such as methyl, ethyl and butyl and aryl groups such as phenyl, which contain any of the foregoing groups of atoms.

The group represented by $R^1$ has 4 to 40 carbon atoms, preferably 6 to 35 carbon atoms, and more preferably 8 to 30 carbon atoms as a whole.

$R^2$ is a straight, branched or cyclic $C_{1-8}$ alkyl group or a $C_{6-20}$ aryl group which may be substituted with an alkyl group. Illustrative examples of the straight, branched or cyclic alkyl group include methyl, ethyl, propyl, isopropyl, n-butyl, sec-butyl, tert-butyl, tert-amyl, n-pentyl, n-hexyl, cyclopentyl, cyclohexyl, cyclopentylmethyl, cyclopentylethyl, cyclohexylmethyl, and cyclohexylethyl. Illustrative examples of the unsubstituted or alkyl-substituted aryl group include phenyl, methylphenyl, naphthyl, anthryl, phenanthryl, and pyrenyl.

$R^3$ to $R^{12}$ are independently hydrogen, or straight, branched or cyclic $C_{1-15}$ alkyl groups which may be substituted with a group of atoms selected from among a halogen atom, hydroxyl, alkoxy, aryloxy, formyl, alkylcarbonyl, arylcarbonyl, carboxy, alkoxycarbonyl, aryloxycarbonyl, cyano, amino, alkylamino, arylamino, mercapto, alkylthio, arylthio, carbamoyl, alkylcarbamoyl, arylcarbamoyl, alkylcarbonylamino, arylcarbonylamino, sulfo, oxo, and imino group. A pair of $R^3$ and $R^4$, a pair of $R^3$ and $R^5$, a pair of $R^4$ and $R^6$, a pair of $R^5$ and $R^6$, a pair of $R^5$ and $R^7$, a pair of $R^5$ and $R^{10}$, a pair of $R^5$ and $R^{11}$, a pair of $R^6$ and $R^8$, a pair of $R^6$ and $R^{11}$, a pair of $R^7$ and $R^8$, a pair of $R^7$ and $R^9$ a pair of $R^7$ and $R^{11}$, a pair of $R^8$ and $R^{11}$, a pair of $R^9$ and $R^{10}$, a pair of $R^9$ and $R^{11}$, and a pair of $R^{10}$ and $R^{11}$ each may form a ring. When these R's in pair form a ring, they are independently straight, branched or cyclic $C_{1-15}$ alkylene groups which may be substituted with a group of atoms selected from among a halogen atom, hydroxyl, alkoxy, aryloxy, formyl, alkylcarbonyl, arylcarbonyl, carboxy, alkoxycarbonyl, aryloxycarbonyl, cyano, amino, alkylamino, arylamino, mercapto, alkylthio, arylthio, carbamoyl, alkylcarbamoyl, arylcarbamoyl, alkylcarbonylamino, arylcarbonylamino, sulfo, oxo, and imino group. A pair of $R^3$ and $R^5$, a pair of $R^5$ and $R^{11}$, a pair of $R^7$ and $R^{11}$, and a pair of $R^9$ and $R^{11}$ may form a single bond so that a double bond is formed between the carbon and the carbon to which these R's are attached.

Examples of the group of atoms are the same as described for $R^1$.

In formula (1), n is an integer of 1 to 8, and preferably 1 to 6. Further preferably, n is equal to 1, 2, 3 or 4.

Illustrative examples of the ester compound according to the invention are those shown below as well as those shown in Examples though not limited thereto.

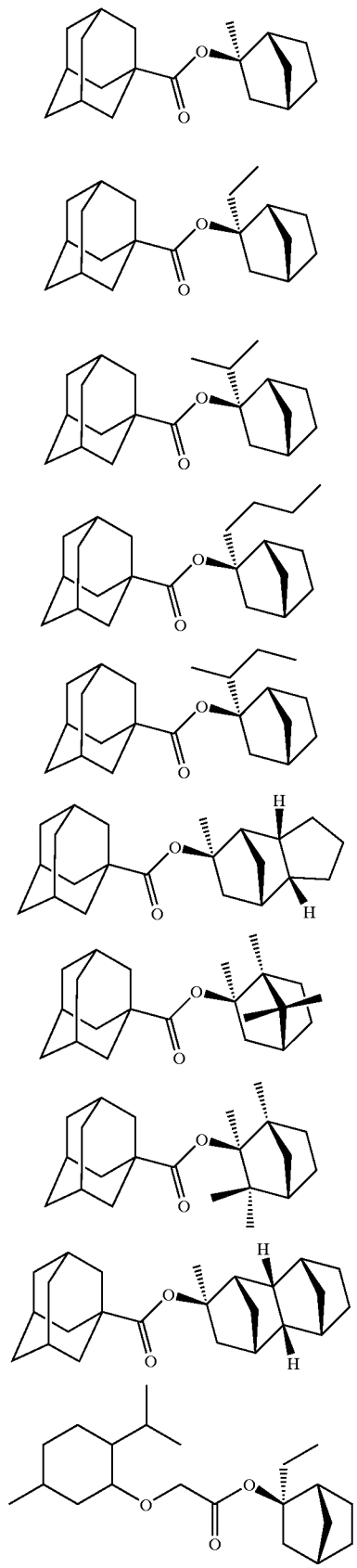

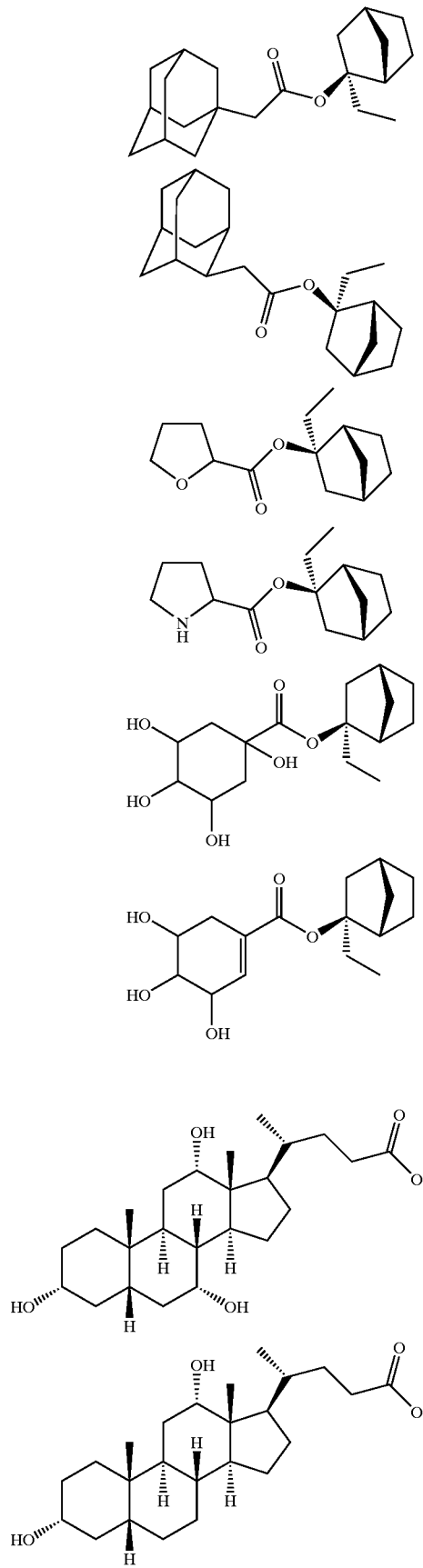
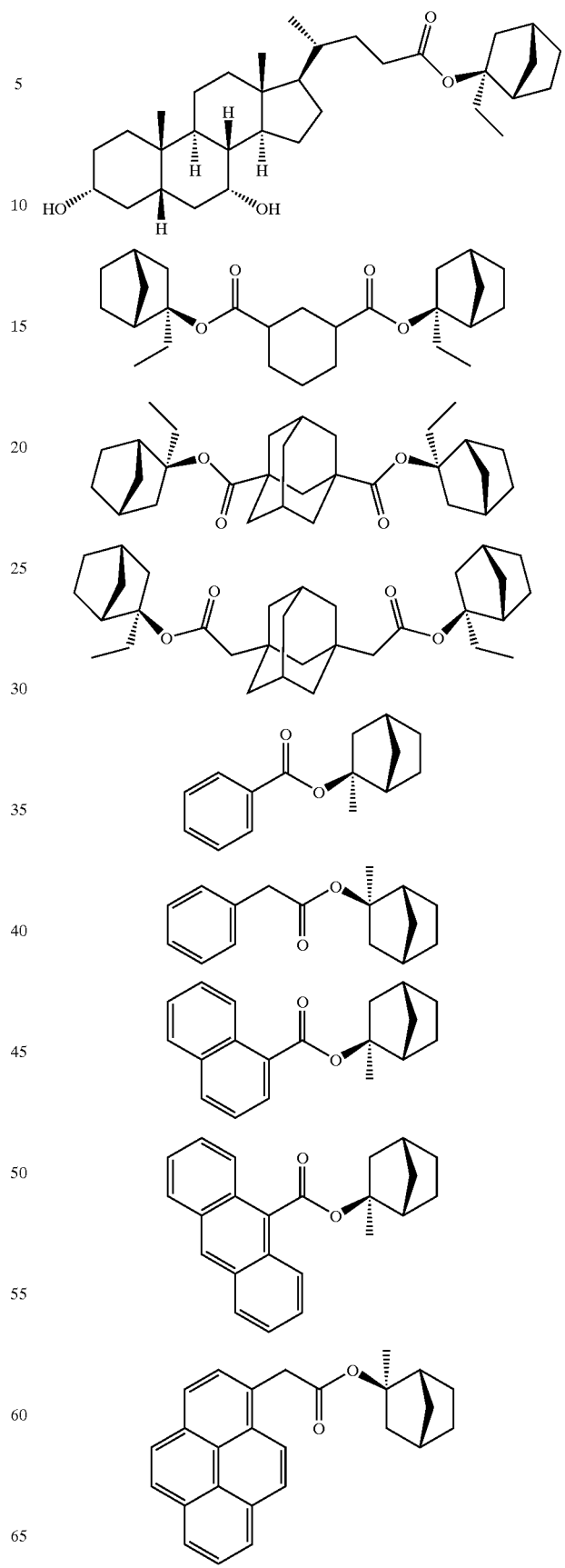

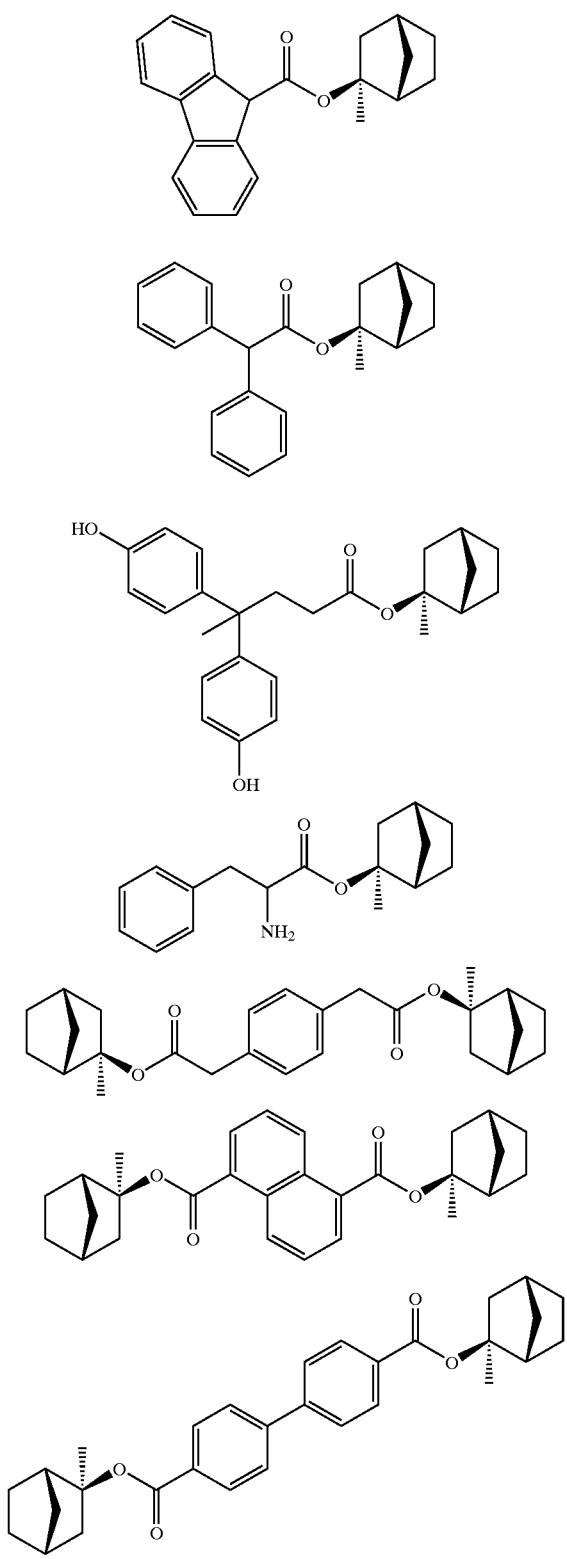

The ester compounds of the invention can be prepared, for example, by the following procedure although the invention is not limited thereto.

Herein, $R^1$ to $R^{12}$ and n are as defined above although $R^3$ to $R^{12}$ and n are omitted for the brevity of description. $R^{2'}$ is identical with $R^2$ except that one hydrogen atom is eliminated from the carbon at the bond position. M represents a metal, HX an acid, OH a base, [O] an oxidizing agent, and [H] a reducing agent.

The first step is to effect nucleophilic addition reaction to the carbonyl of a bicyclo[2.2.1]heptan-2-one or derivative thereof to convert it into an endo-form alcohol. Illustrative of this step are Grignard reaction and reaction using organic lithium compounds although the reaction involved in this step is not limited thereto. Reaction readily takes place under well-known conditions. Reaction is preferably carried out by mixing the reactants: a ketone compound and an alkyl halide or aryl halide with the metal M such as magnesium or lithium in a solvent such as tetrahydrofuran or diethyl ether and heating or cooling the reaction mixture if desired.

It is noted that only the endo-form alcohol yields from the first step and that the following isomerization step is essential to obtain an exo-form alcohol from which the end exo-form ester is produced.

The second step is to convert the endo-form alcohol from the first step into an exo-form alcohol. Some illustrative, non-limiting, procedures of the second step include (a) substitution reaction accompanied by stereo-inversion using acid HX, followed by alkali hydrolysis or alkali solvolysis; (b) dehydration, and addition of acid HX to the resulting olefin, followed by alkali hydrolysis or alkali solvolysis; and (c) dehydration and epoxidization of the resulting olefin, followed by reductive cleavage of epoxy. Reaction readily takes place under well-known conditions. Illustrative, non-limiting examples of the acid HX include inorganic acids such as hydrochloric acid, aqueous hydrochloric acid, hydrobromic acid, hydroiodic acid, and sulfuric acid, and organic acids such as formic acid, acetic acid, propionic acid, benzoic acid, chloroformic acid, chloroacetic acid, dichloroacetic acid, trichloroacetic acid, fluoroacetic acid, difluoroacetic acid, trifluoroacetic acid, and 3,3,3-trifluoropropionic acid. Illustrative, non-limiting examples of the base OH- include inorganic hydroxides such as sodium hydroxide, lithium hydroxide, potassium hydroxide, and barium hydroxide, inorganic carbonates such as sodium carbonate, sodium hydrogen carbonate, lithium carbonate, and potassium carbonate, and alkoxides such as sodium methoxide, sodium ethoxide, lithium methoxide, lithium ethoxide, lithium tert-butoxide, and potassium tert-butoxide, and organic bases such as diethylamine, triethylamine, tri-n-butylamine and dimethylaniline. Illustrative, non-limiting examples of the oxidizing agent [O] include peracids such as performic acid, peracetic acid, trifluoroperacetic acid, and m-chloroperbenzoic acid, and peroxides such as hydrogen peroxide, dimethyl dioxirane, and tert-butyl hydroperoxide. It is noted that when reaction is effected using the oxidizing agent, a metal salt may be co-present as a catalyst. Illustrative, non-limiting examples of the reducing agent [H] include metal hydrides such as boran, alkylboran, dialkylboran, dialkylsilane, trialkylsilane, sodium hydride, lithium hydride, potassium hydride, and calcium hydride; complex hydride salts such as lithium boron hydride, sodium boron hydride, calcium boron hydride, lithium aluminum hydride, and sodium aluminum hydride; alkoxy complex hydride salts such as lithium trimethoxyaluminum hydride, lithium diethoxyaluminum hydride, lithium tri-tert-butoxyaluminum hydride, RED-AL, and sodium tri-methoxyborohydride; and alkyl complex hydride salts such as lithium triethylborohydride, K-Selectride, and L-Selectride.

The third step is to esterify the exo-form alcohol. Reaction readily takes place under well-known conditions. Reaction is preferably carried out by successively or simultaneously adding the reactants: the exo-form alcohol, a carboxylic acid halide prepared separately, and a base (e.g., triethylamine) in a solvent such as methylene chloride and cooling the reaction mixture if desired.

It is noted that in the third step, $R^1$—(COOH), instead of $R^1$—(COCl)$_n$ may be reacted in the presence of a dehydrating agent such as dicyclohexylcarbodiimide.

The ester compound of the invention is advantageously used as one component, especially a dissolution regulator in a resist material. The resist material to which the inventive compound is applicable may be either positive working or negative working or even positive and negative working. A chemical amplification resist material, especially chemical amplification positive resist material is very useful. The resist material in which the ester compound of the invention is blended may have any well-known composition, typically a composition comprising a base resin, a photoacid generator (i.e., a compound capable of generating an acid upon exposure to high energy radiation or electron beams), and an organic solvent.

The resist material having the ester compound of the invention blended therein lends itself to micropatterning with electron beams or deep-UV rays since it is sensitive to high-energy radiation and has excellent sensitivity, resolution, etching resistance, and storage stability. Especially because of the minimized absorption at the exposure wavelength of an ArF or KrF excimer laser, a finely defined pattern having sidewalls perpendicular to the substrate can easily be formed.

EXAMPLE

Examples of the invention are given below by way of illustration and not by way of limitation.

Ester compounds within the scope of the invention are synthesized by the following procedure.

Example 1

Synthesis of DRR1

In 600 ml of tetrahydrofuran was dissolved 148.5 g of ethyl bromide. Below 60° C., this reaction mixture was added dropwise to 32.4 g of metallic magnesium over one hour. After agitation was continued for 2 hours at room temperature, 110.2 g of bicyclo[2.2.1]heptan-2-one was added dropwise over 45 minutes to the reaction mixture which was kept below 65° C. After agitation was continued for one hour at room temperature, the reaction solution was worked up in a conventional manner. The resulting oily substance was distilled in vacuum, collecting 126.9 g of 2-ethylbicyclo[2.2.1]heptan-2-ol in endo-form. The yield was 90.5%.

In 600 ml of benzene was dissolved 125.0 g of 2-ethylbicyclo[2.2.1]heptan-2ol in endo-form. To the solution was added 8.5 g of p-toluenesulfonic acid monohydrate. This reaction mixture was heated, agitated under reflux for 6 hours while removing water, and subjected to conventional post-treatment. The resulting oily substance was purified by silica gel column chromatography, obtaining 85.9 g of 2-ethylidenebicyclo[2.2.1]heptane. The yield was 78.8%.

In 500 ml of methylene chloride was dissolved 84.0 g of 2-ethylidenebicyclo[2.2.1]heptane. To this solution was added 219.0 g of 65% m-chloroperbenzoic acid. This reaction mixture was agitated for 12 hours at 4° C. and subjected to conventional post-treatment, obtaining an oily substance. This was used in the subsequent reaction without purification.

The oily substance obtained in the above step was dissolved in 200 ml of diethyl ether. With stirring, this solution was added dropwise to a suspension of 26.2 g of aluminum lithium hydride in 200 ml of diethyl ether under ice cooling. The reaction mixture was agitated for a further 2 hours at room temperature and. subjected to conventional post-treatment. The resulting oily substance was distilled in vacuum, obtaining 87.0 g of 2-ethyl-bicyclo[2.2.1]heptan-2-ol in exo-form. The yield was 90.3%.

In 200 ml of methylene chloride was dissolved 35.0 g of 2-ethylbicyclo[2.2.1]heptan-2-ol in exo-form. With stirring, 47.0 g of norbornane-2-carboxylic acid chloride and then 54.4 g of triethylamine were added dropwise to the solution under ice cooling. The reaction mixture was agitated for a further 12 hours at room temperature and subjected to conventional post-treatment. The resulting oily substance was distilled in vacuum, collecting 54.9 g of 2-ethylbicyclo[2.2.1]heptan-2-yl norbornane-2-car exo-form, designated DRR1. The yield was 83.3%.

$^1$H-NMR (270 MHz): d=0.80 (3H, t), 1.00–2.05 (17H, m), 2.05–2.65 (6H, m)

IR: n=2962, 2871, 1724, 1187, 1168, 1132, 1114 cm$^{-1}$

Example 2

Synthesis of DRR2

As above, 2-ethylbicyclo[2.2.1]heptan-2-yl 1-adamantanecarboxylate in exo-form, designated DRR2, was synthesized from bicyclo[2.2.2]heptan-2-one.

$^1$H-NMR (270 MHz): d=0.78 (3H, t), 1.05 (1H, m), 1.18 (1H, m), 1.25–1.60 (4H, m), 1.60–2.05 (18H, m), 2.10–2.30 (2H, m), 2.54 (1H, m)

IR (KBr): n=2964, 2933, 2906, 2850, 1716, 1452, 1325, 1267, 1223, 1221, 1174, 1103, 1078 cm$^{-1}$

Example 3

Synthesis of DRR3

As above, 8-methyltricyclo[5.2.1.0$^{2.6}$]decan-8-yl 1-adamantanecarboxylate in exo-form, designated DRR3, was synthesized from tricyclo[5.2.1.0$^{2.6}$]decan-8-one.

$^1$H-NMR (270 MHz): d=0.79 (3H, d), 0.85–1.45 (6H, m), 1.60–2.05 (23H, m), 2.16 (1H, dq), 2.34 (1H, m)

IR (KBr): n=2935, 2904, 2852, 1716, 1452, 1326, 1267, 1236, 1234, 1211, 1161, 1103, 1076 cm$^{-1}$

Example 4

Synthesis of DRR4

As above, 2-ethylbicyclo[2.2.1]heptan-2-yl cholate in exo-form, designated DRR4, was synthesized from bicyclo[2.2.1]heptan-2-one.

$^1$H-NMR (270 MHz): d=0.66 (3H, s), 0.80 (3H, t), 0.87 (3H, s), 0.90–2.05 (35H, m), 2.05–2.35 (6H, m), 2.51 (1H, m), 3.42 (1H, m), 3.81 (1H, m), 3.95 (1H, m)

IR (KBr): n=3435, 2964, 2937, 2870, 1726, 1464, 1377, 1329, 1311, 1267, 1223, 1194, 1171, 1078, 1045 cm$^{-1}$

Example 5

Synthesis of DRR5

As above, 2-ethylbicyclo[2.2.1]heptan-2-yl triformylcholate in exo-form, designated DRR5, was synthesized from bicyclo[2.2.1]heptan-2-one.

$^1$H-NMR (270 MHz): d=0.74 (3H, s), 0.81 (3H, t), 0.93 (3H, s), 1.00–2.30 (38H, m), 2.50 (1H, m), 4.70 (1H, m), 5.06 (1H, m), 5.25 (1H, m), 8.01 (1H, s), 8.09 (1H, s), 8.14 (1H, s)

IR (KBr): n=2964, 2875, 1720, 1465, 1378, 1250, 1248, 1182 cm$^{-1}$

Example 6

Synthesis of DRR6

As above, 2-ethylbicyclo[2.2.1]heptan-2-yl 1-adamantaneacetate in exo-form, designated DRR6, was synthesized from bicyclo[2.2.1]heptan-2-one.

$^1$H-NMR (270 MHz): d=0.82 (3H, t), 1.05 (1H, m), 1.20 (1H, m), 1.30–1.80 (18H, m), 1.90–2.05 (6H, m), 2.21 (1H, m), 2.28 (1H, dq), 2.50 (1H, m)

IR (KBr): n=2964, 2902, 2848, 1722, 1454, 1328, 1261, 1197, 1174, 1130, 1101 cm$^{-1}$

Examples 7–14

Synthesis of DRR7–14

DRR7 to DRR14 were synthesized by the same procedure as above.

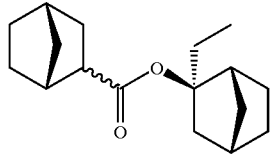

DRR 1

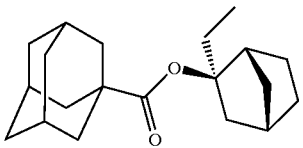

DRR 2

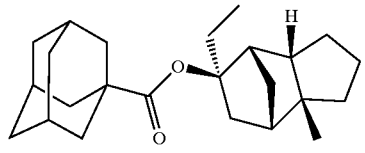

DRR 3

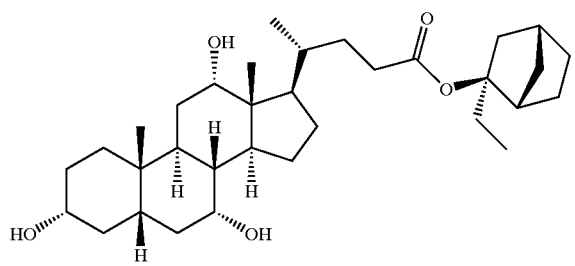

DRR 4

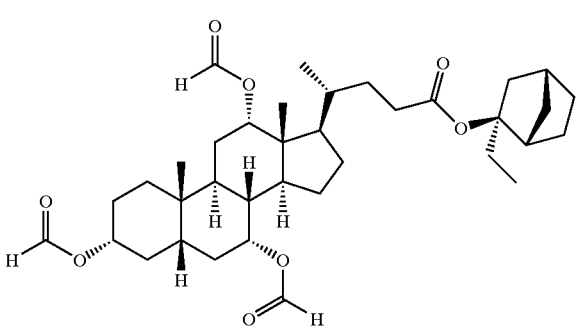

DRR 5

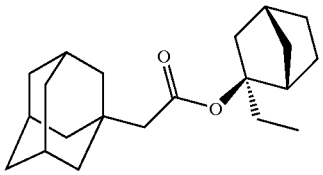

DRR 6

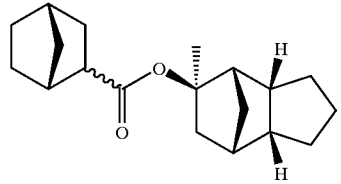

DRR 7

-continued

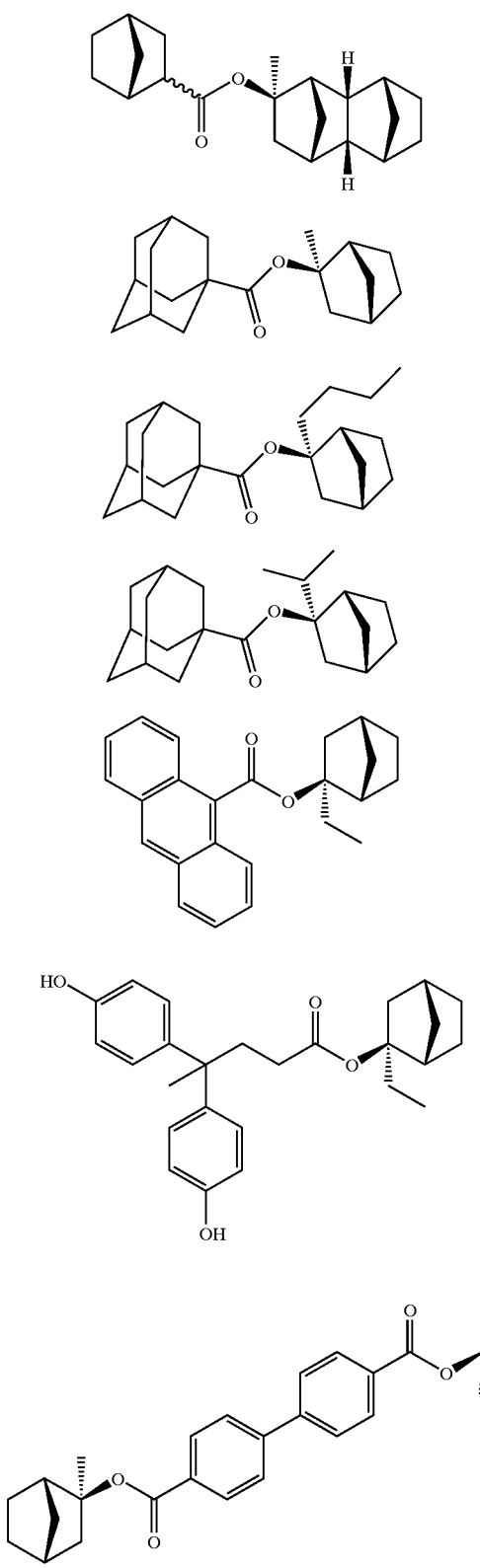

Reference Examples and Comparative Reference Examples

The ester compounds DRR1 to DRR14 obtained in the above Examples were formulated into resist materials, whose performance was examined. For comparison purposes, a similar resist material without the ester compound was formulated and examined.

The components used herein were a polymer (Polymer 1 to Polymer 12), a photoacid generator (PAG1 to PAG8), a dissolution regulator (DRR15 to DRR18), a compound having a ≡C—COOH group in the molecule (ACC1 and ACC2), and a solvent, which were selected in the combination shown in Tables 1 to 5. The solvent contained 0.05% by weight of surfactant Florade FC-430 (Sumitomo 3M).

The solvents and basic compounds used are as follows.

PGMEA: propylene glycol methyl ether acetate
PG/EL: a mixture of 70% PGMEA and 30% ethyl lactate
TBA: tributylamine
TEA: triethanolamine
TMMEA: trismethoxymethoxyethylamine
TMEMEA: trismethoxyethoxymethoxyethylamine

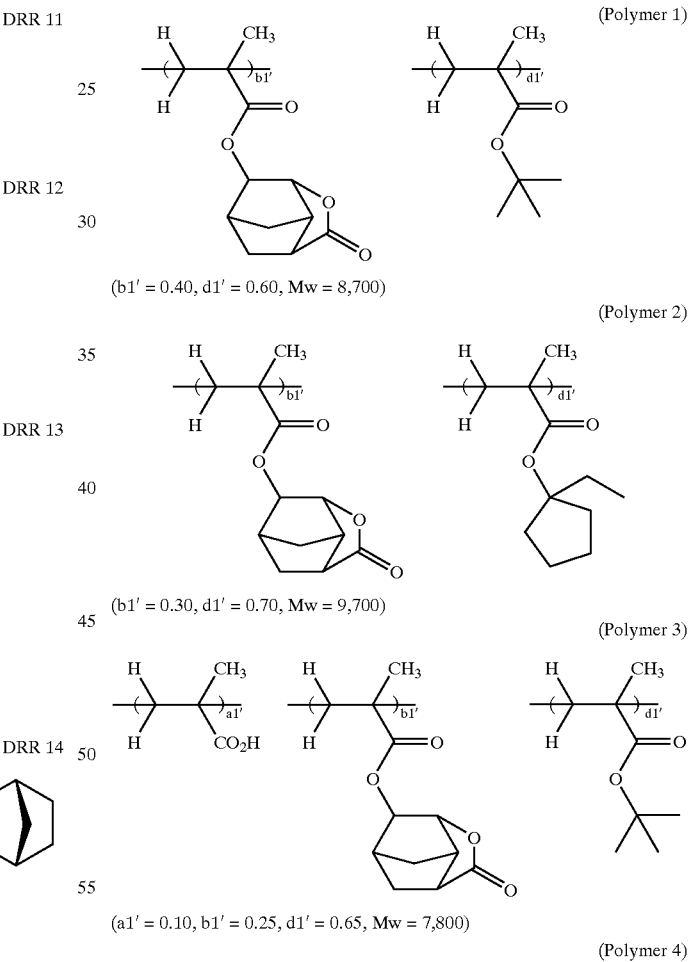

-continued
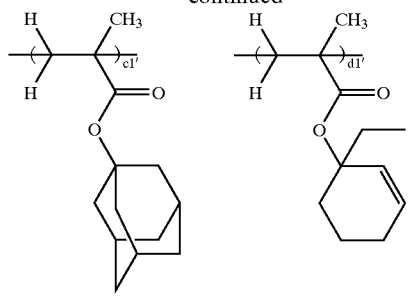
(a1' = 0.10, b1' = 0.20, c1' = 0.30, d1' = 0.40, Mw = 9,300)
(Polymer 5)
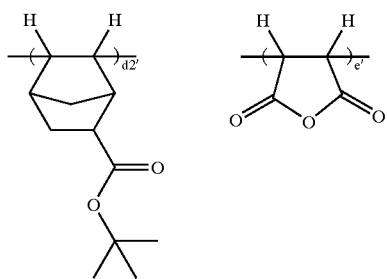
(d2' = 0.50, e' = 0.50, Mw = 11,000)
(Polymer 6)
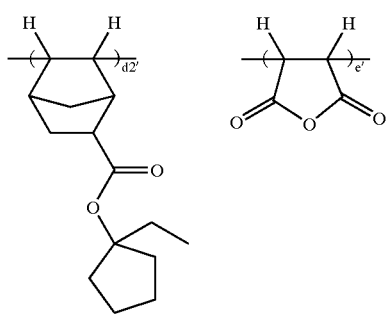
(d2' = 0.50, e' = 0.50, Mw = 12,500)
(Polymer 7)
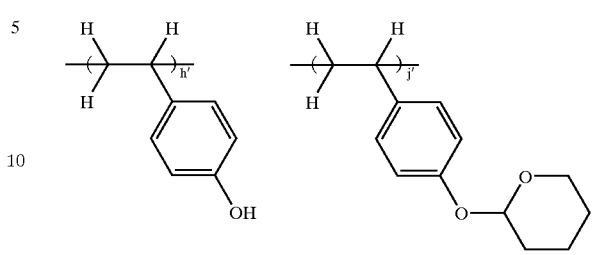
(a2' = 0.10, b2' = 0.30, d2' = 0.60, Mw = 27,600)
(Polymer 8)
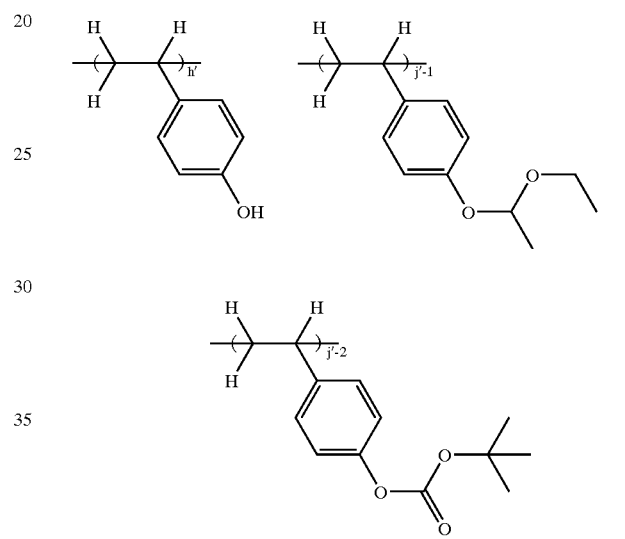
(b3' = 0.40, d3' = 0.60, Mw = 38,400)
-continued
(Polymer 9)
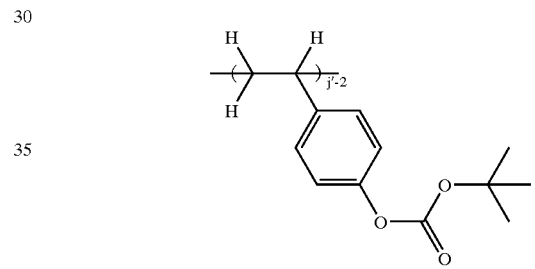
(h' = 0.65, j' = 0.35, Mw = 12,700)
(Polymer 10)
(h' = 0.70, j' - 1 = 0.15, j' - 2 = 0.15, Mw = 12,400)
(Polymer 11)
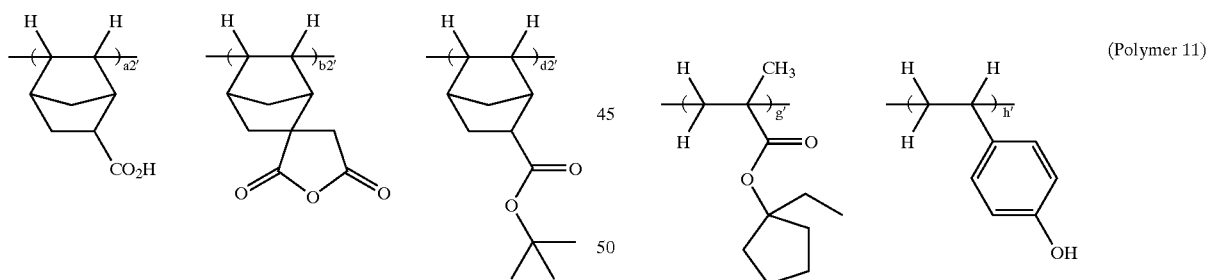
(g' = 0.30, h' = 0.70, Mw = 11,800)
(Polymer 12)
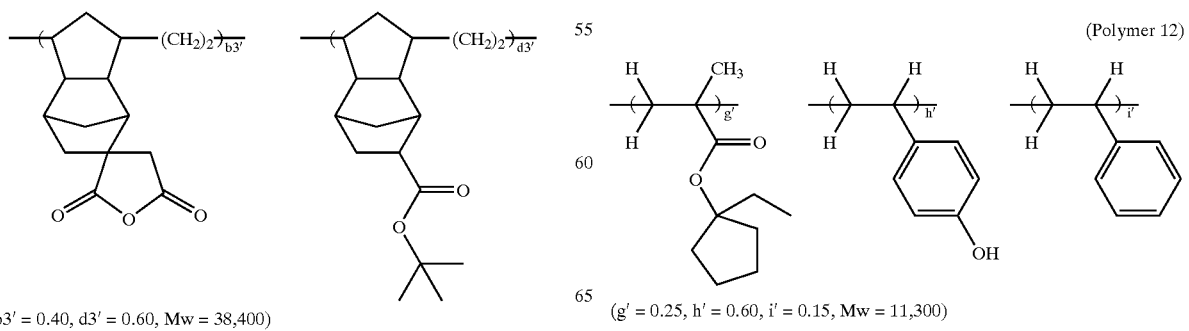
(g' = 0.25, h' = 0.60, i' = 0.15, Mw = 11,300)

-continued

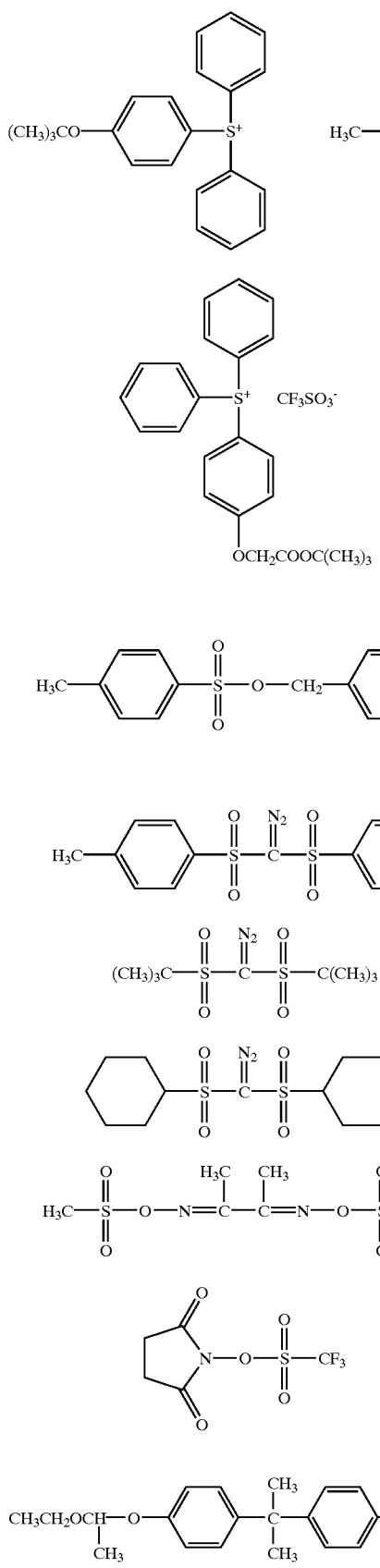

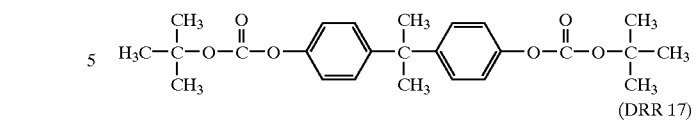

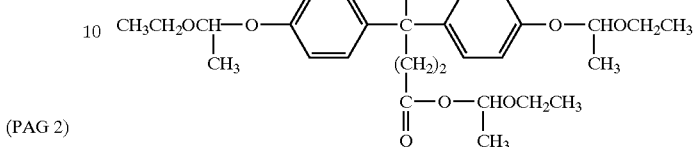

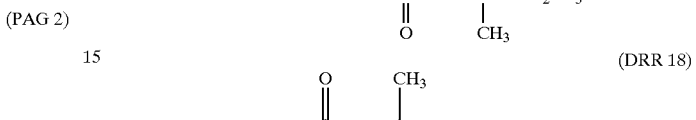

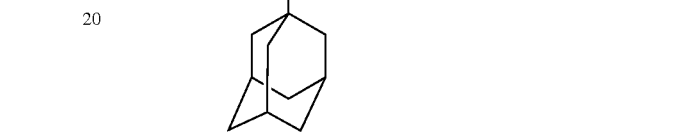

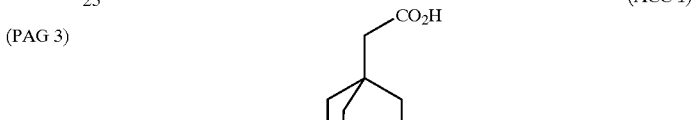

Reference Examples I-1 to I-35

Resist materials were formulated in accordance with the formulation shown in Tables 1 and 2. These materials were each filtered through a 0.2-μm Teflon filter, thereby giving resist solutions. These resist solutions were spin-coated onto silicon wafers, then baked at 110° C. for 90 seconds on a hot plate to give resist films having a thickness of 0.5 μm. The resist films were exposed using an ArF excimer laser stepper (Nikon Corporation; NA 0.55), then baked (PEB) at 110° C. for 90 seconds, and developed with a solution of 2.38% tetramethylammonium hydroxide in water, thereby giving positive patterns.

The resulting resist patterns were evaluated as described below. First, the sensitivity (mJ/cm²) was determined as the dose which provides a 1:1 resolution at the top and bottom of a 0.25 μm line-and-space pattern. The resolution of the resist under evaluation was defined as the minimum line width (μm) of the lines and spaces that separated at this dose. The shape of the resolved resist pattern was examined under a scanning electron microscope.

The composition and test results of the resist materials are shown in Tables 1 and 2.

TABLE 1

| Reference Example | Resin | Photoacid generator | Dissolution regulator | Basic compound | Solvent | Sensitivity | Resolution | shape |
|---|---|---|---|---|---|---|---|---|
| I-1 | Polymer 1 (64) | PAG 1 (2) | DRR 1 (16) | TBA (0.125) | PGMEA (480) | 31.2 | 0.18 | rectangular |
| I-2 | Polymer 1 (64) | PAG 1 (2) | DRR 2 (16) | TBA (0.125) | PGMEA (480) | 31.8 | 0.18 | rectangular |
| I-3 | Polymer 1 (64) | PAG 1 (2) | DRR 3 (16) | TBA (0.125) | PGMEA (480) | 32.1 | 0.18 | rectangular |
| I-4 | Polymer 1 (64) | PAG 1 (2) | DRR 4 (16) | TBA (0.125) | PGMEA (480) | 34.5 | 0.18 | rectangular |
| I-5 | Polymer 1 (64) | PAG 1 (2) | DRR 5 (16) | TBA (0.125) | PGMEA (480) | 32.4 | 0.18 | rectangular |
| I-6 | Polymer 1 (64) | PAG 1 (2) | DRR 6 (16) | TBA (0.125) | PGMEA (480) | 32.4 | 0.18 | rectangular |
| I-7 | Polymer 1 (64) | PAG 1 (2) | DRR 7 (16) | TBA (0.125) | PGMEA (480) | 32.1 | 0.18 | rectangular |
| I-8 | Polymer 1 (64) | PAG 1 (2) | DRR 8 (16) | TBA (0.125) | PGMEA (480) | 31.8 | 0.18 | rectangular |
| I-9 | Polymer 1 (64) | PAG 1 (2) | DRR 9 (16) | TBA (0.125) | PGMEA (480) | 33.0 | 0.18 | rectangular |
| I-10 | Polymer 1 (64) | PAG 1 (2) | DRR 10 (16) | TBA (0.125) | PGMEA (480) | 32.4 | 0.18 | rectangular |
| I-11 | Polymer 1 (64) | PAG 1 (2) | DRR 11 (16) | TBA (0.125) | PGMEA (480) | 30.6 | 0.18 | rectangular |
| I-12 | Polymer 3 (64) | PAG 1 (2) | DRR 2 (16) | TBA (0.125) | PG/EL (480) | 30.6 | 0.18 | rectangular |
| I-13 | Polymer 3 (64) | PAG 2 (2) | DRR 2 (16) | TBA (0.125) | PG/EL (480) | 17.1 | 0.18 | rectangular |
| I-14 | Polymer 3 (64) | PAG 3 (2) | DRR 2 (16) | TBA (0.125) | PG/EL (480) | 29.7 | 0.18 | rectangular |
| I-15 | Polymer 3 (64) | PAG 4 (2) | DRR 2 (16) | TBA (0.125) | PG/EL (480) | 29.3 | 0.18 | rectangular |
| I-16 | Polymer 3 (64) | PAG 5 (2) | DRR 2 (16) | TBA (0.125) | PG/EL (480) | 27.9 | 0.18 | rectangular |
| I-17 | Polymer 3 (64) | PAG 6 (2) | DRR 2 (16) | TBA (0.125) | PG/EL (480) | 28.4 | 0.18 | rectangular |
| I-18 | Polymer 3 (64) | PAG 7 (2) | DRR 2 (16) | TBA (0.125) | PG/EL (480) | 18.0 | 0.18 | rectangular |
| I-19 | Polymer 3 (64) | PAG 8 (2) | DRR 2 (16) | TBA (0.125) | PG/EL (480) | 15.8 | 0.18 | rectangular |
| I-20 | Polymer 2 (32) Polymer 4 (32) | PAG 2 (2) | DRR 7 (16) | TBA (0.125) | PGMEA (480) | 12.0 | 0.18 | rectangular |

TABLE 2

| Reference Example | Resin | Photoacid generator | Dissolution regulator | Basic compound | Solvent | Sensitivity | Resolution | shape |
|---|---|---|---|---|---|---|---|---|
| I-21 | Polymer 2 (32) Polymer 4 (32) | PAG 2 (2) | DRR 7 (16) | TEA (0.125) | PGMEA (480) | 11.4 | 0.15 | rectangular |
| I-22 | Polymer 2 (32) Polymer 4 (32) | PAG 2 (2) | DRR 7 (16) | TMMEA (0.125) | PGMEA (480) | 10.8 | 0.18 | rectangular |
| I-23 | Polymer 2 (32) Polymer 4 (32) | PAG 2 (2) | DRR 7 (16) | TMEMEA (0.125) | PGMEA (480) | 10.5 | 0.18 | rectangular |
| I-24 | Polymer 5 (76) | PAG 7 (2) | DRR 4 (4) | TEA (0.125) | PGMEA (480) | 34.5 | 0.20 | T-top |
| I-25 | Polymer 5 (72) | PAG 7 (2) | DRR 4 (8) | TEA (0.125) | PGMEA (480) | 33.6 | 0.18 | slight T-top |
| I-26 | Polymer 5 (64) | PAG 7 (2) | DRR 4 (16) | TEA (0.125) | PGMEA (480) | 31.5 | 0.15 | rectangular |
| I-27 | Polymer 5 (56) | PAG 7 (2) | DRR 4 (24) | TEA (0.125) | PGMEA (480) | 30.9 | 0.18 | rectangular |
| I-28 | Polymer 6 (64) | PAG 8 (2) | DRR 5 (8) DRR 15 (8) | TEA (0.125) | PGMEA (480) | 13.5 | 0.20 | some positive taper |

TABLE 2-continued

| Reference Example | Resin | Photoacid generator | Dissolution regulator | Basic compound | Solvent | Sensitivity | Resolution | shape |
|---|---|---|---|---|---|---|---|---|
| I-29 | Polymer 6 (64) | PAG 8 (2) | DRR 5 (8) DRR 16 (8) | TEA (0.125) | PGMEA (480) | 14.4 | 0.20 | some positive taper |
| I-30 | Polymer 6 (64) | PAG 8 (2) | DRR 5 (8) DRR 17 (8) | TEA (0.125) | PGMEA (480) | 12.9 | 0.20 | some positive taper |
| I-31 | Polymer 6 (64) | PAG 8 (2) | DRR 5 (8) DRR 18 (8) | TEA (0.125) | PGMEA (480) | 10.8 | 0.18 | rectangular |
| I-32 | Polymer 7 (64) | PAG 2 (2) | DRR 5 (16) | TEA (0.125) | PGMEA (480) | 18.0 | 0.18 | rectangular |
| I-33 | Polymer 7 (64) | PAG 2 (2) | ORR 5 (16) ACC 1 (4) | TEA (0.125) | PGMEA (480) | 17.4 | 0.15 | rectangular |
| I-34 | Polymer 8 (64) | PAG 2 (2) | DRR 5 (8) DRR 1 (8) | TEA (0.125) | PGMEA (480) | 19.5 | 0.10 | rectangular |
| I-35 | Polymer 8 (64) | PAG 2 (2) | DRR 5 (8) DRR 2 (8) | TEA (0.125) | PGMEA (480) | 18.9 | 0.18 | rectangular |

Comparative Reference Examples I-1 to I-4

Resist materials were similarly formulated in accordance with the formulation shown in Table 3 and examined for performance. The composition and test results of the resist materials are shown in Table 3.

TABLE 3

| Comparative Reference Example | Resin | Photoacid generator | Dissolution regulator | Basic compound | Solvent | Sensitivity | Resolution | shape |
|---|---|---|---|---|---|---|---|---|
| I-1 | Polymer 1 (64) | PAG 1 (2) | DRR 15 (16) | TBA (0.125) | PGMEA (480) | 44.5 | 0.22 | positive taper |
| I-2 | Polymer 1 (64) | PAG 1 (2) | DRR 16 (16) | TBA (0.125) | PGMEA (480) | 47.3 | 0.22 | positive taper |
| I-3 | Polymer 1 (64) | PAG 1 (2) | DRR 17 (16) | TBA (0.125) | PGMEA (480) | 43.1 | 0.22 | positive taper |
| I-4 | Polymer 1 (64) | PAG 1 (2) | DRR 18 (16) | TBA (0.125) | PGMEA (480) | 37.7 | 0.20 | rectangular |

Reference Examples II-1 to II-20

Resist materials were formulated in accordance with the formulation shown in Table 4. These materials were each filtered through a 0.2-μm Teflon filter, thereby giving resist solutions. These resist solutions were spin-coated onto silicon wafers, then baked at 110° C. for 90 seconds on a hot plate to give resist films having a thickness of 0.7 μm. The resist films were exposed using a KrF excimer laser stepper (Nikon Corporation; NA 0.5), then baked (PEB) at 110° C. for 90 seconds, and developed with a solution of 2.38% tetramethylammonium hydroxide in water, thereby giving positive patterns.

The resulting resist patterns were evaluated as described below. First, the sensitivity (mJ/cm$^2$) was determined as the dose which provides a 1:1 resolution at the top and bottom of a 0.30 μm line-and-space pattern. The resolution of the resist under evaluation was defined as the minimum line width (μm) of the lines and spaces that separated at this dose. The shape of the resolved resist pattern was examined under a scanning electron microscope.

The composition and test results of the resist materials are shown in Table 4.

TABLE 4

| Comparative Reference Example | Resin | Photoacid generator | Dissolution regulator | Basic compound | Solvent | Sensitivity | Resolution | shape |
|---|---|---|---|---|---|---|---|---|
| II-1 | Polymer 9 (64) | PAG 1 (2) | DRR 12 (16) | TEA (0.125) | PG/EL (480) | 42.3 | 0.22 | rectangular |
| II-2 | Polymer 9 (64) | PAG 1 (2) | DRR 13 (16) | TEA (0.125) | PG/EL (480) | 40.1 | 0.22 | rectangular |
| II-3 | Polymer 9 (64) | PAG 1 (2) | DRR 14 (16) | TEA (0.125) | PG/EL (480) | 38.5 | 0.22 | rectangular |
| II-4 | Polymer 9 (64) | PAG 2 (2) | DRR 13 (16) | TEA (0.125) | PG/EL (480) | 32.3 | 0.22 | rectangular |
| II-5 | Polymer 10 (64) | PAG 2 (2) | DRR 13 (16) | TEA (0.125) | PG/EL (480) | 33.5 | 0.22 | rectangular |
| II-6 | Polymer 11 (64) | PAG 2 (2) | DRR 13 (16) | TEA (0.125) | PG/EL (480) | 30.7 | 0.20 | rectangular |

TABLE 4-continued

| Comparative Reference Example | Resin | Photoacid generator | Dissolution regulator | Basic compound | Solvent | Sensitivity | Resolution | shape |
|---|---|---|---|---|---|---|---|---|
| II-7 | Polymer 12 (64) | PAG 2 (2) | DRR 13 (16) | TEA (0.125) | PG/EL (480) | 31.2 | 0.22 | rectangular |
| II-8 | Polymer 10 (76) | PAG 4 (2) | DRR 14 (4) | TEA (0.125) | PGMEA (480) | 45.4 | 0.26 | T-top |
| II-9 | Polymer 10 (72) | PAG 4 (2) | DRR 14 (8) | TEA (0.125) | PGMEA (480) | 43.7 | 0.24 | slight T-top |
| II-10 | Polymer 10 (64) | PAG 4 (2) | DRR 14 (16) | TEA (0.125) | PGMEA (480) | 41.2 | 0.22 | rectangular |
| II-11 | Polymer 10 (56) | PAG 4 (2) | DRR 14 (24) | TEA (0.125) | PGMEA (480) | 40.7 | 0.22 | rectangular |
| II-12 | Polymer 9 (64) | PAG 5 (2) | DRR 13 (16) | TEA (0.125) | PGMEA (480) | 42.7 | 0.22 | rectangular |
| II-13 | Polymer 9 (64) | PAG 5 (2) | DRR 13 (8) DRR 12 (8) | TEA (0.125) | PGMEA (480) | 43.3 | 0.22 | rectangular |
| II-14 | Polymer 9 (64) | PAG 5 (2) | DRR 13 (8) DRR 14 (8) | TEA (0.125) | PGMEA (480) | 41.7 | 0.20 | rectangular |
| II-15 | Polymer 9 (64) | PAG 5 (2) | DRR 13 (8) DRR 15 (8) | TEA (0.125) | PGMEA (480) | 42.1 | 0.22 | rectangular |
| II-16 | Polymer 9 (64) | PAG 5 (2) | DRR 13 (8) DRR 16 (8) | TEA (0.125) | PGMEA (480) | 45.1 | 0.22 | rectangular |
| II-17 | Polymer 9 (64) | PAG 5 (2) | DRR 13 (8) DRR 17 (8) | TEA (0.125) | PGMEA (480) | 42.0 | 0.22 | rectangular |
| II-18 | Polymer 9 (64) | PAG 5 (2) | DRR 13 (8) DRR 18 (8) | TEA (0.125) | PGMEA (480) | 40.9 | 0.22 | rectangular |
| II-19 | Polymer 9 (64) | PAG 5 (2) | DRR 13 (16) ACC 1 (4) | TEA (0.125) | PGMEA (480) | 41.5 | 0.22 | rectangular |
| II-20 | Polymer 9 (64) | PAG 5 (2) | DRR 13 (16) ACC 2 (4) | TEA (0.125) | PGMEA (480) | 40.3 | 0.20 | rectangular |

Comparative Reference Examples II-1 to II-4

Resist materials were similarly formulated in accordance with the formulation shown in Table 5 and examined for performance. The composition and test results of the resist materials are shown in Table 5.

TABLE 5

| Comparative Reference Example | Resin | Photoacid generator | Dissolution regulator | Basic compound | Solvent | Sensitivity | Resolution | shape |
|---|---|---|---|---|---|---|---|---|
| II-1 | Polymer 9 (64) | PAG 1 (2) | DRR 15 (16) | ThA (0.125) | PG/EL (480) | 45.9 | 0.26 | rectangular |
| II-2 | Polymer 9 (64) | PAG 1 (2) | DRR 16 (16) | TEA (0.125) | PG/EL (480) | 47.7 | 0.26 | some positive taper |
| II-3 | Polymer 9 (64) | PAG 1 (2) | DRR 17 (16) | TEA (0.125) | PG/EL (480) | 45.0 | 0.26 | rectangular |
| II-4 | Polymer 9 (64) | PAG 1 (2) | DRR 18 (16) | TEA (0.125) | PG/EL (480) | 44.5 | 0.26 | rectangular |

It is evident from Tables 1 to 5 that the resist materials having the ester compounds of the invention blended therein show a higher sensitivity and resolution than the resist materials having the prior art dissolution regulators blended therein.

Japanese Patent Application No. 11-138090 are incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

What is claimed is:

1. An exo-form ester compound of the following general formula (1):

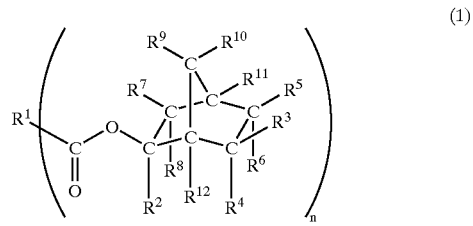

wherein $R^1$ is selected from among (i) alicyclic saturated hydrocarbons selected from the group consisting of:

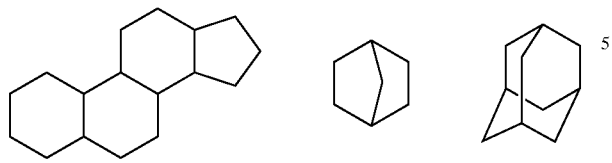

(ii) hydrocarbons belonging to (i) in which at least one hydrogen atom at an arbitrary position is replaced by a straight, branched or cyclic alkyl, (iii) hydrocarbons belonging to (i) and (ii) in which a carbon-carbon bond at an arbitrary position is unsaturated to introduce at least one aromatic ring, (iv) hydrocarbons belonging to (i) to (iii) in which at least one $CH_2$, CH or C at an arbitrary position is replaced by O, N, NH, S, SO or $SO_2$, and (v) hydrocarbons belonging to (i) to (iv) in which at least one hydrogen atom at an arbitrary position is replaced by a group of atoms selected from among a halogen atom, hydroxyl, alkoxy, aryloxy, formyl, formyloxy, alkylcarbonyl, arylcarbonyl, carboxy, alkoxycarbonyl, aryloxycarbonyl, cyano, amino, alkylamino, arylamino, mercapto, alkylthio, arylthio, carbamoyl, alkylcarbamoyl, arylcarbamoyl, alkylcarbonylamino, arylcarbonylamino, sulfo, oxo, and imino group, or an alkyl or aryl containing said group of atoms; $R^2$ is a straight, branched or cyclic alkyl group of 1 to 8 carbon atoms or a substituted or unsubstituted aryl group of 6 to 20 carbon atoms; $R^3$ to $R^{12}$ each are hydrogen or a monovalent hydrocarbon group of 1 to 15 carbon atoms which may contain a hetero atom or $R^3$ to $R^{12}$, taken together, may form a ring, and when they form a ring, $R^3$ to $R^{12}$ may, independently, represent divalent hydrocarbon groups of 1 to 15 carbon atoms which may contain a hetero atom, or two of $R^3$ to $R^{12}$ which are attached to adjacent carbon atoms may directly bond together to form a double bond; and n is an integer of 1 to 8, with the proviso that the formula also represents an enantiomer.

2. The exo-form ester compound of claim 1 wherein in formula (1), $R^2$ is a straight, branched or cyclic alkyl group of 1 to 8 carbon atoms or an aryl group of 6 to 20 carbon atoms which may be substituted with an alkyl group, $R^3$ to $R^{12}$ are independently hydrogen, or straight, branched or cyclic alkyl groups of 1 to 15 carbon atoms which may be substituted with a group of atoms selected from among a halogen atom, hydroxyl, alkoxy, aryloxy, formyl, alkylcarbonyl, arylcarbonyl, carboxy, alkoxycarbonyl, aryloxycarbonyl, cyano, amino, alkylamino, arylamino, mercapto, alkylthio, arylthio, carbamoyl, alkylcarbamoyl, arylcarbamoyl, alkylcarbonylamino, arylcarbonylamino, sulfo, oxo, and imino group, a pair of $R^3$ and $R^4$, a pair of $R^3$ and $R^5$, a pair of $R^4$ and $R^6$, a pair of $R^5$ and $R^6$, a pair of $R^5$ and $R^7$, a pair of $R^5$ and $R^{10}$, a pair of $R^5$ and $R^{11}$, a pair of $R^6$ and $R^8$, a pair of $R^6$ and $R^{11}$, a pair of $R^7$ and $R^8$, a pair of $R^7$ and $R^9$, a pair of $R^7$ and $R^{11}$, a pair of $R^8$ and $R^{11}$, a pair of $R^9$ and $R^{10}$, a pair of $R^9$ and $R^{11}$, and a pair of $R^{10}$ and $R^{11}$ each may form a ring, and when they form a ring, they are independently straight, branched or cyclic alkylene groups of 1 to 15 carbon atoms which may be substituted with a group of atoms selected from among a halogen atom, hydroxyl, alkoxy, aryloxy, formyl, alkylcarbonyl, arylcarbonyl, carboxy, alkoxycarbonyl, aryloxycarbonyl, cyano, amino, alkylamino, arylamino, mercapto, alkylthio, arylthio, carbamoyl, alkylcarbamoyl, arylcarbamoyl, alkylcarbonylamino, arylcarbonylamino, sulfo, oxo, and imino group, or a pair of R3 and R5 may form

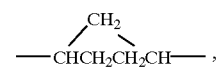

or a pair of $R^3$ and $R^5$, a pair of $R^5$ and $R^{11}$, a pair of $R^7$ and $R^{11}$, and a pair of $R^9$ and $R^{11}$ may form a single bond so that a double bond is formed between the carbon and the carbon to which these R's are attached.

3. An exo-form ester compound according to claim 1, wherein $R^1$ is the moiety:

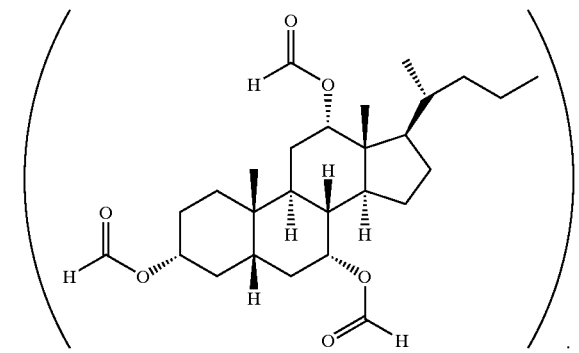

4. An exo-form ester compound of the formula:

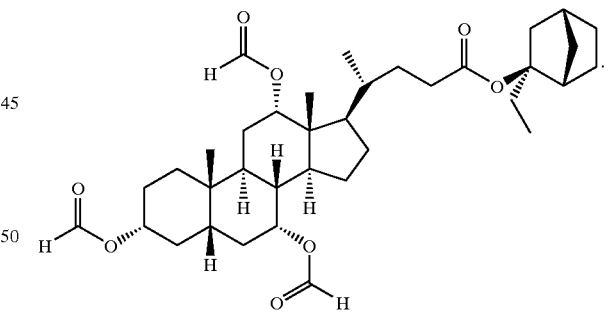

5. An exo-form ester compound of the formula (1):

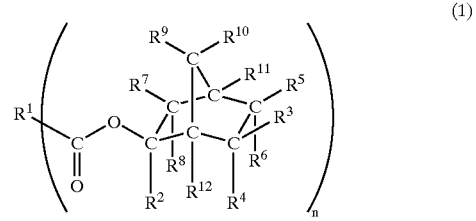

(1)

wherein $R^1$ is a moiety of the formula:

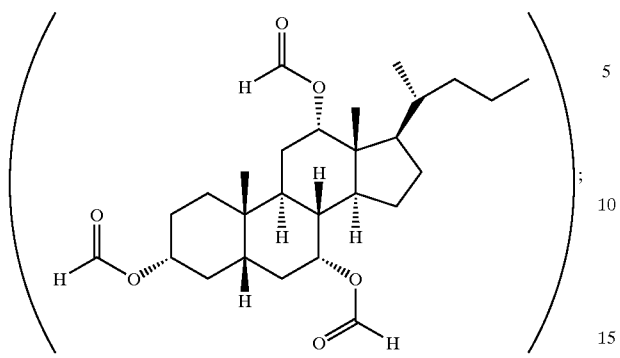

$R^2$ is a straight, branched or cyclic alkyl group of 1 to 8 carbon atoms or a substituted or unsubstituted aryl group of 6 to 20 carbon atoms; $R^3$ to $R^{12}$ each are hydrogen or a monovalent hydrocarbon group of 1 to 15 carbon atoms which may contain a hetero atom or $R^3$ to $R^{12}$, taken together, may form a ring, and when they form a ring, they represent divalent hydrocarbon groups of 1 to 15 carbon atoms which may contain a hetero atom, or two of $R^3$ to $R^{12}$ which are attached to adjacent carbon atoms may directly bond together to form a double bond; and n is an integer of 1 to 8, with the proviso that the formula also represents an enantiomer.

\* \* \* \* \*